United States Patent [19]

Kodama et al.

[11] Patent Number: 5,441,932
[45] Date of Patent: Aug. 15, 1995

[54] SUGAR COMPOUNDS FOR INHIBITION OF THE BIOSYNTHESIS OF SUGAR CHAINS CONTAINING SIALIC ACID

[75] Inventors: Hisashi Kodama; Hironobu Hashimoto; Yasuhiro Kajihara, all of Kanagawa, Japan

[73] Assignee: Japan Tobacco, Inc., Tokyo, Japan

[21] Appl. No.: 25,051

[22] Filed: Mar. 2, 1993

[30] Foreign Application Priority Data

Mar. 3, 1992 [JP] Japan .................................. 4-045419

[51] Int. Cl.$^6$ ................... A61K 31/70; A61K 31/715; A61K 31/72; A61K 31/73
[52] U.S. Cl. ........................................ 514/8; 514/25; 514/53; 514/54; 514/62; 530/300; 530/322; 530/350; 530/367; 530/386; 530/395; 536/17.2; 536/17.5; 536/18.7; 536/53; 536/54; 536/55.2; 536/63; 536/66; 536/84; 536/92; 536/123.13
[58] Field of Search ..................... 514/53, 54, 62, 8.25; 536/17.2, 4.1, 18.7, 55.2, 17.5, 53, 54, 63, 66, 84.92, 123.13; 530/300, 322, 350, 367, 386, 395

[56] References Cited

U.S. PATENT DOCUMENTS 5,211,937   5/1993   Brandley ................................ 424/1.1

FOREIGN PATENT DOCUMENTS 0353910   2/1970   European Pat. Off. .
0146090   6/1985   European Pat. Off. .

OTHER PUBLICATIONS

Rana et al. *Carbohydr. Res.* 1983, 117, 101–111.
Good et al. *Vox Sang.* 1992, 62, 180–189.
Lemieux et al. *Carbohydr. Res.* 1988, 293–305.
Zurabyan et al. *Bioorg. Khim.* 1978, 4(5), 654–665.
Kamiya et al. *Argic. Biol. Chem.* 1987, 51(4), 1195–1197.
Shaban et al. *Carbohydr. Res.* 1971, 20, 399–405.
Jacquinet et al. *J. Chem. Soc. Perkin Trans. I* 1979, 2, 319–322.
Fukuda et al. *Biochim. Biophys. Acta* 1984, 801, 1–9.
Ayouba et al. *Glycoconj. J.* 1992, 9, 141–147.
Conboy et al. *J. Am. Soc. Mass Spectrom.* 1992, 3, 804–814.
Jacquinet et al. *Carbohydr. Res.* 1975, 42, 251–258.
Phillips et al, Science, vol. 250, pp. 1130–1131 (1990).
Walz et al, Science, vol. 250, pp. 1132–1135 (1990).
Lowe et al, Cell, vol. 63, pp. 475–484 (1990).
Tyrell et al, Proc. Natl. Acad. Sci. USA, vol. 88, pp. 10372–10376 (1991).
Wong et al, Can. J. Chem., vol. 62, pp. 1207–1213 (1984).
Michalski et al, Chemical Abstracts, vol. 115, Abstract No. 90297x (1991).
Sabesan et al, J. Am. Chem. Soc., vol. 108, pp. 2068–2080 (1986).
Smith et al, The Journal of Biological Chemistry, vol. 255, No. 1, pp. 55–59 (1980).
Amano et al, The Journal of Biological Chemistry, vol. 266, No. 18, pp. 11461–11477 (1991).
Hanaoka et al, The Journal of Biological Chemistry, vol. 264, No. 17, pp. 9842–9849 (1989).
Shabaev et al, Chemical Abstracts, vol. 97, Abstract No. 90362 (1982).
Spencer et al, Chemical Abstracts, vol. 78, Abstract No. 94229 (1973).

*Primary Examiner*—Douglas W. Robinson
*Assistant Examiner*—Kathleen Kahler Fonda
*Attorney, Agent, or Firm*—Birch, Stewart, Kolasch & Birch

[57] ABSTRACT

An inhibitor of the biosynthesis of sugar chains containing sialic acid that is excellent in the suppression of inflammation or allergy, which comprises as an active ingredient a sugar compound of the formula (1):

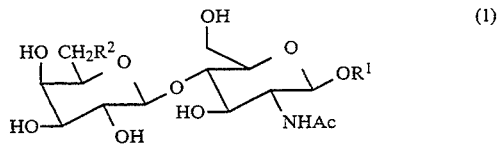

wherein $R^1$ is a hydrogen atom, a substituted or unsubstituted aliphatic hydrocarbon group, a substituted or unsubstituted aromatic hydrocarbon group, a peptide residue or a glycoprotein, and $R^2$ is a hydrogen atom, a sulfhydryl group, an acyloxy group, an acylthio group, an aryloxy group, an alkyloxy group or a glycothio residue. The inhibitor of the biosynthesis of sugar chains containing sialic acid may be used as a therapeutic agent for inflammation caused by sugar chains containing sialic acid.

15 Claims, No Drawings

SUGAR COMPOUNDS FOR INHIBITION OF THE BIOSYNTHESIS OF SUGAR CHAINS CONTAINING SIALIC ACID

BACKGROUND OF THE INVENTION

1. Field of the Invention

The present invention relates to a novel sugar compound for inhibiting the biosynthesis of sugar chains containing sialic acid, which are known as the allergy, inflammation, or the like, and to an inhibitor of the biosynthesis of sugar chains containing sialic acid, wherein the inhibitor contains the novel sugar compound of the present invention as an active ingredient.

2. Description of the Related Background Art

It is reported that the sugar chains containing sialic acid and existing in a surface layer of leukocyte contribute to the occurrence of inflammation or allergy when the leukocyte invades a tissue (see M. L. Phillips et al., Science, 250, 1130, (1990); G. Walz et al., Science, 250, 1132, (1990); J. B. Lowe et al., Cell, 63,475, (1990)). In detail, the first step of inflammation or allergy occurs when the leukocyte invades the tissue and the sugar chains containing sialic acid and existing in the surface layer of the leukocyte adhere to an endothelial cell of the blood vessel. If the sugar chains containing sialic acid could be removed from the leukocyte, the leukocyte would fail to adhere to the endothelial cell of the blood vessel, to invade the tissue. As a result, the inflammation and the allergy would be suppressed.

There is, however, no previously known compound that selectively inhibits the biosynthesis of sugar chains containing sialic acid. Therefore, it has been desired to have an effective inhibitor of the biosynthesis of sugar chains containing sialic acid.

SUMMARY OF THE INVENTION

The inventors have extensively and intensively studied the above circumstances, and have found that a specific compound can selectively inhibit the biosynthesis of sugar chains containing sialic acid. The present invention is based on such a new finding. It is an object of the present invention to provide an excellent inhibitor of the biosynthesis of sugar chains containing sialic acid.

The object of the present invention can be achieved by a sugar compound of the formula (1):

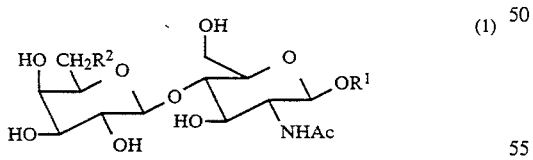

wherein $R^1$ is a hydrogen atom, a substituted or unsubstituted aliphatic hydrocarbon group, a substituted or unsubstituted aromatic hydrocarbon group, a peptide residue or a sugar residue, and $R^2$ is a hydrogen atom, a sulfhydryl group, an acyloxy group, an acylthio group, an aryloxy group, an alkyloxy group, a sugar residue or a glycothio residue.

In the above formula the aliphatic hydrocarbon group for $R^1$ may be preferably $C_1$-$C_5$ hydrocarbons, and more preferably $C_1$-$C_3$ hydrocarbons.

Specifically, $R^1$ is preferably methyl, a hydrogen atom, ovalbumin, fetuin, glycophorin, or α2-macroglobulin, and $R^2$ is preferably a hydrogen atom, a tetrahydropyranyl group, or a sulfhydryl group.

The sugar compound according to the present invention may be produced, for example, by the following process. In detail, the process comprises reacting, for example, 6-deoxy-α-D-galactose-tetraacetate with a crystalline phosphoric acid to obtain a compound of the formula (2), 6-deoxy-D-galactose-monophosphoric acid:

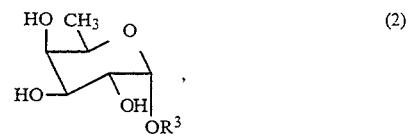

wherein $R^3$ is a phosphoric acid residue or a phosphate residue; reacting the compound of formula (2) with morpholidate uridine 5′-monophosphate to obtain a compound of the formula (3), uridine 5′-diphosphoric acid-6-deoxy-D-galactose:

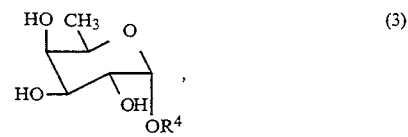

wherein $R^4$ is an uridine 5′-diphosphoric acid residue or an uridine 5′-diphosphate residue; and then reacting the compound of formula (3) with an N-acetylglucosamine derivative or a glycoprotein by means of a galactose transfer enzyme to obtain the sugar compound according to the present invention.

The sugar compound may also be produced by another process as follows. In detail, the sugar compound according to the present invention may be produced by the method, which comprises a step of partially introducing a protecting group to a hydroxyl group of methyl-β-N-acetyllactosamine to obtain methyl-2-acetamide-3, 6-di-O-acetyl-2-deoxy-4-O-(2, 3, 4-tri-O-acetyl-β-D-galactopyranosyl)-β-D-glucopyranoside of the formula (7):

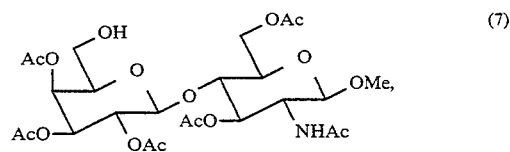

a step of reacting dihydropyran or thioacetate thereto, and a step of then removing the protecting group therefrom.

A suitable protecting group is acetyl.

The present invention involves all novel intermediates present in the above production processes.

For example, novel intermediates in the first process as described above are as follows:

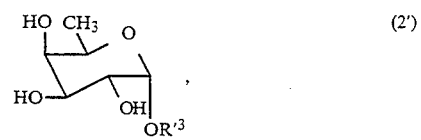

wherein R'³ is a phosphoric acid residue, a phosphate residue, an uridine 5'-diphosphoric acid residue, an uridine 5'-diphosphate residue, or their salt.

The sugar compound according to the present invention can effectively inhibit the biosynthesis of the sugar chains containing sialic acid, so that the invasion of the leukocyte into the tissue, which might otherwise be promoted by sugar chains containing sialic acid, may be suppressed to restrict the inflammation and the allergy. Therefore, the sugar compound according to the present invention can be used as an antiinflammatory agent for curing inflammation in a communicable disease, as well as an inhibitor of the biosynthesis of sugar chains containing sialic acid.

A composition for inhibiting the biosynthesis of sugar chains containing sialic acid according to the present invention comprises an effective amount to inhibit the biosynthesis of sugar chains containing sialic acid of the above sugar compound as an active ingredient, and a pharmaceutically acceptable carrier.

An antiinflammatory agent according to the present invention comprises an effective amount to prevent or reduce inflammation of the above sugar compound as an active ingredient, and a pharmaceutically acceptable carrier.

The appropriate daily dosage of the composition for inhibiting the biosynthesis of sugar chains containing sialic acid or the antiinflammatory agent containing the sugar compound according to the present invention may be properly determined depending upon the symptoms of the patient, and is usually 1 to 100 mg per Kg of weight. The route of administration may be via perlingual administration, hypodermic injection, sinus injection, or local administration. There is no specific restriction on the route of administration. The composition for inhibiting the biosynthesis of sugar chains containing sialic acid or the antiinflammatory agent may be formed as drugs in the usual manner by intermixing with a pharmaceutically acceptable carrier or solvent, for example, as an oral medicine in the form of a powdered drug, tablet, granules, and capsules or as a local application agent in the form of injection and paste.

The sugar compound of the present invention may effectively restrict the enzyme activity of the sialyltransferase, so that it may show an excellent inhibition effect with respect to the biosynthesis of sugar chains containing sialic acid.

The sugar compound according to the present invention shows high inhibition activity with respect to the biosynthesis of sugar chains containing sialic acid, and therefore is effective as a therapeutic agent against communicable disease, inflammation, or the like caused by the sugar chains containing sialic acid.

Further objects and advantages of the present invention will be apparent from the description of the preferred embodiments of the invention.

DESCRIPTION OF THE PREFERRED EMBODIMENTS

EXAMPLE 1

5 g of 6-deoxy-α(or β)-D-galactose-tetraacetate and 5 g of crystalline phosphoric acid thoroughly dried were heated to 50° C. under reduced pressure by means of a vacuum pump, and stirred for 2 hours to obtain a reaction solution. Then, this reaction solution was dissolved in 30 ml of tetrahydrofuran and added to 240 ml of a 1N lithium hydroxide aqueous solution under cooling with ice. The resulting solution was left to stand at room temperature overnight and precipitates were filtered off. The filtrate was passed through an anion-exchange resin column (Dowex-50) to remove lithium ions and, with addition of 10 ml of 1.5N aqueous ammonia, concentrated under reduced pressure to obtain 3.5 g of an ammonium salt of the intermediate a of the formula (2) (6-deoxy-D-galactose-monophosphoric acid).

The physical properties of the intermediate a (ammonium salt) are as follows:

State: White solid

Solubility: Soluble in water, alkaline solutions, acid solutions, and various buffer solutions. Hardly soluble in organic solvents.

Molecular formula: $C_6H_{11}O_8P(NH_4)_2$ ¹H-NMR, δ(ppm), $D_2O$, TSP; 1.15(d, 3H), 3.67(ddd, 1H), 3.76(d, 1H), 3.86(dd, 1H), 4.20(q, 1H), 5.38(dd, 1H) ¹³C-NMR, δ(ppm), $D_2O$, TSP; 16.0, 69.6, 71.0, 72.1, 74.5, 96.8.

Added to 10 ml of anhydrous pyridine were 300 mg of the intermediate a (ammonium salt) obtained in the above step and 700 mg of morpholidate uridine 5'-monophosphate thoroughly dried, which were stirred at room temperature for 3 days. The reaction solution thus obtained was concentrated under reduced pressure and dissolved in 20 ml of water. The solution was stirred thoroughly with 20 ml of ethyl ether, and was subject to liquid separation. The aqueous phase thus obtained was adsorbed on an anion-exchange resin (Dowex-2, CT type, 2×20 cm) column and subjected to fractional elution while continuously increasing the concentration by using as eluate 1 l of a 0.01M sodium chloride aqueous solution containing 0.003N hydrochloric acid and 1 l of a 1M sodium chloride aqueous solution. Activated carbon was added to a crude fraction obtained by putting together fractions showing ultraviolet absorption at a wavelength of 254 nm, which were stirred at room temperature for 2 hours for adsorption. The activated carbon was collected by filtration and washed thoroughly with water, followed by eluation with 50% ethanol containing 0.03N ammonia. The ethanol solution obtained by filtration was concentrated under reduced pressure to obtain 350 mg of an ammonium salt of the intermediate b of the formula (3) (uridine 5'-diphosphate-6-deoxy-D-galactose).

The physical properties of the intermediate b (ammonium salt) are as follows:

State: White solid

Solubility: Soluble in water, alkaline solutions, and various buffer solutions. Decomposed in acid. Hardly soluble in organic solvents.

Molecular formula: $C_{15}H_{24}N_2O_{16}P_2(NH_4)_2$ ¹H-NMR, δ(ppm), $D_2O$, TSP; 1.18(d, 3H), 3.72(ddd, 1H), 3.79(d, 1H), 3.89(dd, 1H), 5.53(dd, 1H), 5.94(d, 1H), 7.93(d, 1H).

82 mg of the above intermediate b (ammonium salt) and 50 mg of methyl-2-acetamide-2-deoxy-β-D-glucopyranoside were dissolved in 9 ml of 0.1M HEPES buffer solution (pH 6.5) containing 20 mM of manganese chloride, and, with addition of 4.5 units of galactosyltranferase commercially available from Sigma Inc., the mixture was left to stand at 37° C. for 3 days for reaction. The reaction solution was passed through an activated carbon column (2×13 cm) for adsorption. Then the column was subject to eluation with 50% ethanol. The obtained eluate fraction was concentrated to obtain 100 mg of crude product. The crude product was separated and purified using a column (3×81.2 cm) filled with Sephadex G-15 from Pharmacia Inc. with a mobile phase of water to obtain 50 mg of methyl-2-acetamide- 2-deoxy-4-O-(6-deoxy-$\beta$-D-galactopyranosyl)-$\beta$-D-glucopyranoside (sugar compound A), which was a sugar compound represented by the aforementioned formula (1) in which $R^1$ is methyl and $R^2$ is hydrogen.

The physical properties of the sugar compound A are as follows:
State: White solid
Solubility: Soluble in water, alkaline solutions, acid solutions, various buffer solutions, methanol, and ethanol. Hardly soluble in hexane and in chloroform.
Molecular formula: $C_{15}H_{27}NO_{10}$ $^1$H-NMR, $\delta$(ppm), $D_2O$, TSP; 1.21(d, 3H), 2.00(s, 3H), 3.47(s, 3H), 4.39(d, 1H), 4.43(d, 1H).

EXAMPLE 2

82 mg of a sodium salt of the intermediate b obtained in Example 1 and 43 mg of 2-acetamide-2-deoxy-D-glucose were dissolved in 8.5 ml of 0.1M HEPES buffer solution (pH 6.5) containing 20 mM of manganese chloride, and, with addition of 4 units of galactosyltranferase commercially available from Sigma Inc., the mixture was left to stand at 37° C. for 3 days for reaction. The reaction solution was passed through an activated carbon column (2×13 cm) for adsorption. Then the column was subject to elution with 50% ethanol. The obtained eluate fraction was concentrated to obtain 70 mg of crude product. The crude product was separated and purified using a column (3×81.2 cm) filled with Sephadex G-15 from Pharmacia Inc. with a mobile phase of water to obtain 20 mg of mixture of $\alpha$- and $\beta$-2-acetamide-2-deoxy-4-O-(6-deoxy-$\beta$-D-galactopyranosyl)-D-glucose (sugar compound B), which was a sugar compound represented by the aforementioned formula (1) in which $R^1$ is hydrogen and $R^2$ is also hydrogen.

The physical properties of the sugar compound B are as follows:
State: White solid
Solubility: Soluble in water, alkaline solutions, acid solutions, various buffer solutions, methanol, and ethanol. Hardly soluble in hexane and in chloroform.
Molecular formula: $C_{14}H_{25}NO_{10}$ $^1$H-NMR, $\delta$(ppm), $D_2O$, TSP; 1.25(d, 3H), 2.04(s, 3H), 4.42(d, 1H), 5.19(s, 0.7H).

EXAMPLE 3

100 mg of a sodium salt of the intermediate b obtained in Example 1 and 10 mg of glycoprotein ovalbumin were dissolved in 1 ml of 0.1M HEPES buffer solution (pH 6.5) containing 20 mM of manganese chloride, and, with addition of 1 unit of galactosyltranferase commercially available from Sigma Inc., the mixture was left to stand at 37° C. for 3 days for reaction. The reaction solution was separated and purified using a column (3×81.2 cm) filled with Sephadex G-15 from Pharmacia Inc. with a mobile phase of water then to be freeze-dried to obtain 9 mg of 2-acetamide-2-deoxy-4-O-(6-deoxy-$\beta$-D-galactopyranosyl)-$\beta$-D-glucopyranosylated ovalbumin (sugar compound C), which was a sugar compound represented by the aforementioned formula (1) in which $R^1$ is ovalbumin and $R^2$ is hydrogen.

The physical properties of the sugar compound C are as follows:
State: White solid
Solubility: Soluble in water and various buffer solutions. Hardly soluble in organic solvents.
Molecular weight: 45000

EXAMPLE 4

The same process was carried out as in Example 3 except that 10 mg of asialoagalactofetuin was used in place of 10 mg of glycoprotein ovalbumin. Obtained was 8 mg of 2-acetamide-2-deoxy-4-O-( 6-deoxy-$\beta$-D-galactopyranosyl)-$\beta$-D-glucopyranosylated fetuin (sugar compound D), which was a sugar compound represented by the aforementioned formula (1) in which $R^1$ is fetuin and $R^2$ is hydrogen.

The physical properties of the sugar compound D are as follows:
State: White solid
Solubility: Soluble in water and various buffer solutions. Hardly soluble in organic solvents.
Molecular weight: 43000

EXAMPLE 5

The same process was carried out as in Example 3 except that 20 mg of asialoagalactoglycophorin was used in place of 10 mg of glycoprotein ovalbumin. Obtained was 8 mg of 2-acetamide-2-deoxy-4-O-(6-deoxy-$\beta$-D-galactopyranosyl)-$\beta$-D-glucopyranosylated glycophorin (sugar compound E), which was a sugar compound represented by the aforementioned formula (1) in which $R^1$ is glycophorin and $R^2$ is hydrogen.

The physical properties of the sugar compound E are as follows:
State: White solid
Solubility: Soluble in water and various buffer solutions. Hardly soluble in organic solvents.
Molecular weight: 48000

EXAMPLE 6

The same process was carried out as in Example 3 except that 10 mg of asialoagalacto $\alpha$2-macroglobulin was used in place of 10 mg of glycoprotein ovalbumin. Obtained was 8 mg of 2-acetamide-2-deoxy-4-O-(6-deoxy-$\beta$-D-galactopyranosyl)-$\beta$-D-glucopyranosylated $\alpha$2-macroglobulin (sugar compound F), which was a sugar compound represented by the aforementioned formula (1) in which $R^1$ is $\alpha$2-macroglobulin and $R^2$ is hydrogen.

The physical properties of the sugar compound F are as follows:
State: White solid
Solubility: Soluble in water and various buffer solutions. Hardly soluble in organic solvents.
Molecular weight: 800000

EXAMPLE 7

530 mg of methyl-$\beta$-N-acetyllactosamine was added to 10 ml of dimethylformamide containing 568 mg of benzaldehyde dimethyl acetal and 238 mg of camphor sulfonic acid. The mixture was stirred at 60° C. for 3 hours, and neutralized with triethylamine. Then the resultant mixture was concentrated under reduced pressure. The concentrate was acetylated in the usual manner, and purified through a silica gel column chromatography (ethyl acetate: methanol=9:1) to obtain 845 mg of the intermediate c (methyl-2-acetamide-3, 6-di-O-acetyl-2-deoxy-4-O-(2,3-di-O-acetyl-4, 6-O-benzylidene-$\beta$-D-galactopyranosyl)-$\beta$-D-glucopyranoside), which was represented by the following formula (4).

(4)

[Structure of intermediate c with Ph, OAc, OMe, AcO, NHAc groups]

The physical properties of the intermediate c are as follows:
State: White solid
Solubility: Soluble in chloroform, methanol, and ethanol. Hardly soluble in water and various buffer solutions.
$^1$H-NMR, $\delta$(ppm), CDCl$_3$, TMS; 1.95(s,3H), 2.04(s, 3H), 2.05(s, 3H), 2.07(s, 3H), 2.12(s, 3H), 3.45(s, 3H), 3.80(t, 1H), 4.90(dd, 1H), 5.09(dd, 1H), 5.27(dd, 1H), 5.48(s, 1H), 5,89(d, 1H).

464 mg of the above intermediate c was added in 60% acetic acid aqueous solution, and the mixture was stirred at 80° C. for 2 hours for reaction. The reaction solution was concentrated under reduced pressure, and purified through a silica gel column chromatography (ethyl acetate: methanol=4:1) to obtain 394 mg of methyl-2-acetamide-3, 6-di-O-acetyl-2-deoxy-4-O-(2, 3-di-O-acetyl-$\beta$-D-galactopyranosyl)-$\beta$-D-glucopyranoside (intermediate d), which was represented by the following formula (5).

(5)

[Structure of intermediate d with OH, OAc, OMe, HO, AcO, NHAc groups]

The physical properties of the intermediate d are as follows:
State: White solid
Solubility: Soluble in chloroform, methanol, and ethanol. Hardly soluble in water and various buffer solutions.
$^1$H-NMR, $\delta$(ppm), CDCl$_3$, TMS; 1.97(s 3H), 2.07(s, 6H), 2.10(s, 3H), 2.11(s, 3H), 4.41(d, 1H), 4.49(dd, 1H), 4.55(d, 1H), 4.91(dd, 1H), 5.07(dd, 1H), 5.25(dd, 1H), 6.30(d, 1H).

229 mg of the above intermediate d was dissolved in 2 ml of dimethylformamide containing 165 mg of t-butyldimethylsilylchloride and 183 mg of imidazole, and the mixture was stirred at room temperature for fifteen minutes. Then 250 $\mu$l of methanol was added to the mixture, and the mixture was concentrated under reduced pressure. The concentrate was acetylated in the usual manner, and then purified through a silica gel column chromatography (ethyl acetate) to obtain 229 mg of methyl-2-acetamide-3, 6-di-O-acetyl-2-deoxy-4-O-(2, 3, 4-tri-O-acetyl-6-O-t-butyldimethylsilyl-$\beta$-D-galactopyranosyl)-$\beta$-D-glucopyranoside (intermediate e), which was represented by the following formula (6).

(6)

[Structure of intermediate e with R$^5$, OAc, OMe, AcO, NHAc groups]

where R$^5$ is a t-butyldimethylsilyloxy group.
The physical properties of the intermediate e are as follows:
State: White solid
Solubility: Soluble in chloroform, methanol, and ethanol. Hardly soluble in water and various buffer solutions.
$^1$H-NMR, $\delta$(ppm), CDCl$_3$, TMS; 0.85(s, 9H), 1.97(s, 3H), 1.98(s, 3H), 2.06(s, 3H), 2.07(s, 3H), 2.11(s, 3H), 2.13(s, 3H), 3.45(s, 3H), 3.81(t, 1H), 4.14(dd, 1H), 4.36(d, 1H), 4.48(d, 1H), 4.51(dd, 1H), 5.01(dd, 1H), 5.06(dd, 1H), 5.11(dd, 1H), 5.47(d, 1H), 5.86(d, 1H).

267 mg of the above intermediate e was added in 60% acetic acid aqueous solution, and stirred at 90° C. for thirty minutes for reaction. The reaction solution was concentrated under reduced pressure, and purified through a silica gel column chromatography (ethyl acetate: methanol=19:1) to obtain 171 mg of methyl-2-acetamide-3, 6-di-O-acetyl-2-deoxy-4-O-(2, 3, 4-tri-O-acetyl-$\beta$-D-galactopyranosyl)-$\beta$-D-glucopyranoside (intermediate f), which was represented by the aforementioned formula (7).

The physical properties of the intermediate f are as follows:
State: White solid
Solubility: Soluble in chloroform, methanol, and ethanol. Hardly soluble in water and various buffer solutions.
$^1$H-NMR, $\delta$(ppm), CDCl$_3$, TMS; 1.99(s, 6H), 2.07(s, 3H), 2.09(s, 3H), 2.11(s, 3H), 2.16(s, 3H), 3.45(s, 3H), 3,84(t, 1H), 4.40(d, 1H), 4.51(dd, 1H), 4.57(d, 1H), 5.03(dd, 1H), 5.10(t, 1H), 5.14(dd, 1H), 5.37(d, 1H), 5.96(d, 1H).

55 mg of the above intermediate f was added in 1 ml of methylene chloride containing 41 $\mu$l of 2, 3-dihydropyrane and a catalytic amount of pyridinium-p-toluenesulfonic acid, and stirred at room temperature for 2.5 hours for reaction. The reaction solution was added in 5 ml of saturated sodium bicarbonate solution, and was subject to three extractions with 5 ml of chloroform. The chloroform extracting layer was concentrated under reduced pressure, and purified through a silica gel column chromatography (ethyl acetate: methanol=19:1) to obtain 46 mg of methyl-2-acetamide-3, 6-di-O-acetyl-2-deoxy-4-O-(2, 3, 4-tri-O-acetyl-6-O-tetrahydropyranyl-$\beta$-D-galactopyranosyl)-$\beta$-D-glucopyranoside (intermediate g), which was represented by the following formula (8).

(8)

[Structure of intermediate g with R$^6$, OAc, OMe, AcO, NHAc groups]

where R$^6$ is a tetrahydropyranyloxy group.
The physical properties of the intermediate g are as follows.
State: White solid Solubility: Soluble in chloroform, methanol, and ethanol. Hardly soluble in water and various buffer solutions.

$^1$H-NMR, δ(ppm), CDCl$_3$, TMS; 1.98(s, 9H), 2.04(s, 3H), 2.06(s, 6H), 2.07(s, 6H), 2.12(s, 6H), 2.14(s, 6H), 3.45(s, 6H), 4.35(d, 2H), 4.61(dd, 1H), 5.44(d, 1H), 5.47(d, 1H), 5.73(d, 1H), 5.74(d, 1H).

The acetyl group was detached from 15 mg of the intermediate g with sodium methylate in the usual manner, and purified through a gel permeation chromatography (Sephadex G-15, 3×81.2 cm) to obtain 5 mg of methyl-2-acetamide-2-deoxy-4-O-(6-O-tetrahydropyranyl-β-D-galactopyranosyl)-β-D-glucopyranoside (sugar compound G), which was a sugar compound represented by the aforementioned formula (1) in which R$^1$ is a methyl group and R$^2$ is a tetrahydropyranyl group.

The physical properties of the sugar compound G are as follows:
State: White solid
Solubility: Soluble in water, alkaline solutions, acid solutions, various buffer solutions, methanol, and ethanol. Hardly soluble in hexane and in chloroform.
$^1$H-NMR, δ(ppm), D$_2$O, TSP; 1.98(s, 3H), 3.47(s, 3H), 4.43(d, 2H).

EXAMPLE 8

55 mg of the intermediate f obtained in Example 7 was subject to tosylation with p-toluene sulfonilchloride in pyridine in the usual manner to obtain 53 mg of methyl-2-acetamide-3, 6-di-O-acetyl-2-deoxy-4-O-(2, 3, 4-tri-O-acetyl-6-O-p-toluenesulfonyl-β-D-galactopyranosyl)-β-D-glucopyranoside (intermediate h), which was represented by the following formula (9).

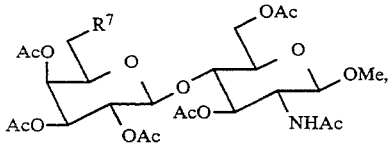

where R$^7$ is a p-toluenesulfonyloxy group.

The physical properties of the intermediate h are as follows:
State: White solid
Solubility: Soluble in chloroform, methanol, and ethanol. Hardly soluble in water and various buffer solutions.

$^1$H-NMR, δ(ppm), CDCl$_3$, TMS; 1.96(s, 3H), 1.98(s, 3H), 2.04(s, 3H), 2.05(s, 3H), 2.06(s, 3H), 2.11(s, 3H), 2.47(s, 3H), 3.46(s, 3H), 3.81(t, 1H), 4.38(d, 1H), 4.96(dd, 1H), 5.08(dd, 1H), 5.11(t, 1H), 5.35(d, 1H), 5.80(d, 1H), 7.38(d, 2H), 7.77(d, 2H).

53 mg of the above intermediate h was added in 1.7 ml of dimethylformamide containing 79 mg of potassium thioacetate, and heated at 80° C. overnight for reaction. The reaction solution was concentrated under reduced pressure, and purified through a silica gel column chromatography (ethyl acetate: methanol=19:1) to obtain 50 mg of methyl-2-acetamide-3, 6-di-O-acetyl-2-deoxy-4-O-(2, 3, 4-tri-O-acetyl-6-S-acetyl-6-deoxy-β-D-galactopyranosyl)-β-D-glucopyranoside (intermediate i), which was represented by the following formula (10).

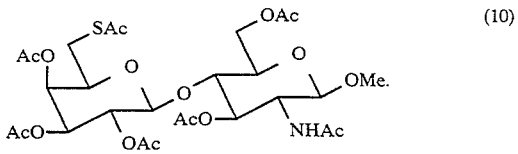

The physical properties of the intermediate i are as follows:
State: White solid
Solubility: Soluble in chloroform, methanol, and ethanol. Hardly soluble in water and various buffer solutions.

$^1$H-NMR, δ(ppm), CDCl$_3$, TMS; 1.97(s, 3H), 1.99(s, 3H), 2.05(s, 3H), 2.11(s, 3H), 2.12(s, 3H), 2.17(s, 3H), 2.35(s, 3H), 3.04(d, 2H), 3.46(s, 3H), 3.82(t, 1H), 4.36(d, 1H), 4.46(d, 1H), 4.51(dd, 1H), 4.95(dd, 1H), 5.08(dd, 1H), 5.10(dd, 1H), 5.39(d, 1H), 5.61(d, 1H).

32 mg of the above intermediate i was treated with 8 ml of 28% aqueous ammonia containing 10 equivalents of dithiothreitol for detachment of the acetyl group, and concentrated under reduced pressure. Then the resultant was purified through a gel permeation chromatography (Sephadex G-15, 3×81.2 cm) to obtain 5 mg of methyl-2-acetamide-2-deoxy-4-O-(6-mercapto-β-D-galactopyranosyl)-β-D-glucopyranoside (sugar compound H), which was a sugar compound represented by the aforementioned formula (1) in which R$^1$ is a methyl group and R$^2$ is a mercapto group.

The physical properties of the sugar compound H are as follows:
State: White solid
Solubility: Soluble in water, alkaline solutions, acid solutions, various buffer solutions, methanol, and ethanol. Hardly soluble in hexane and in chloroform.
$^1$H-NMR, δ(ppm), D$_2$O, TSP; 2.00(s, 3H), 2.70–2.75(m, 2H), 3.47(s, 3H), 4.44(d, 2H).

EXAMPLE 9

The following biological assay was carried out to evaluate inhibition activity with respect to the biosynthesis of sugar chains containing sialic acid of each of the sugar compounds A–H of the present invention obtained in Examples 1 to 8. In other words, the tests were conducted using a test system of the biosynthesis of sialic acid-sugar chains containing sialic acid which was reported by Paulson et al.

A tester solution was prepared containing the following respective reagents in 50 μl of final contents:
100 mM sodium cacodylate buffer solution (pH 6.5);
0.075 nmol cytidine-monophosphate-14C sialic acid;
3 mM β-methyllactosaminide;
50 μg cow serum albumin;
0.5% Triton X-100.

A specimen compound was added in 50 μl of the tester solution, and, with addition of 1×10$^{-6}$ units of β-galactoside-α-2, 6-sialyltransferase commercially available, the mixture was left to stand at 37° C. for 10 minutes. 1 ml of 5 mM phosphoric acid buffer solution was added to stop the reaction. Then the solution was passed through an anion-exchange resin column (Dowex-1X8, phosphoric acid type, 1 ml) to remove unreacted cytidine-monophosphate-14C sialic acid. Further, the column was washed with 1 ml of 5 mM phosphoric acid buffer solution to recover radioactive sialic acid-containing sugar chains. The radioactivity was measured by a liquid scintillation counter.

The thus-measured radioactivity was shown by percentage to the radioactivity of untreated section not including the specimen compound, which was defined as inhibition activity.

The below Table shows the results with 50% inhibition concentrations (M/l) of $\beta$-galactoside-$\alpha$-2, 6-sialyltransferase enzyme activity for each of the sugar compounds according to the present invention. It can be seen from the results that the sugar compounds according to the present invention have extremely inhibition activity with respect to the biosynthesis of sugar chains containing sialic acid.

TABLE

| Specimen compound | 50% activity inhibition concentration |
|---|---|
| Sugar compound A | $0.5 \times 10^{-3}$ M/l |
| Sugar compound B | $2.0 \times 10^{-3}$ M/l |
| Sugar compound C | $1.0 \times 10^{-5}$ M/l |
| Sugar compound D | $4.2 \times 10^{-6}$ M/l |
| Sugar compound E | $2.7 \times 10^{-6}$ M/l |
| Sugar compound F | $1.0 \times 10^{-6}$ M/l |
| Sugar compound G | $1.3 \times 10^{-3}$ M/l |
| Sugar compound H | $4.0 \times 10^{-3}$ M/l |

Many widely different embodiments of the present invention may be constructed without departing from the spirit and scope of the present invention. It should be understood that the present invention is not limited to the specific embodiments described in the specification, except as defined in the appended claims.

What is claimed is:

1. A sugar compound of the formula:

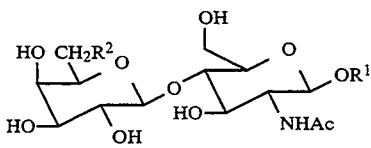

wherein $R^1$ is a hydrogen atom, a substituted or unsubstituted aliphatic hydrocarbon group, a substituted or unsubstituted aromatic hydrocarbon group, a peptide residue or a glycoprotein, and $R^2$ is a hydrogen atom, a sulfhydryl group, an acyloxy group, an acylthio group, an aryloxy group, an alkyloxy group or a glycothio residue.

2. A sugar compound according to claim 1, wherein $R^1$ is methyl or a hydrogen atom.

3. A sugar compound according to claim 1, wherein $R^2$ is a hydrogen atom.

4. A composition for inhibiting the biosynthesis of sugar chains containing sialic acid comprising:
   an effective amount to inhibit the biosynthesis of sugar chains containing sialic acid of the sugar compound of claim 1; and
   a pharmaceutically acceptable carrier.

5. An antiinflammatory agent comprising:
   an effective amount to prevent or reduce inflammation of the sugar compound of claim 1; and
   a pharmaceutically acceptable carrier.

6. A method of inhibiting the biosynthesis of sugar chains containing sialic acid which comprises administering to a patient in need of treatment an effective amount of the compound of claim 1 to inhibit the biosynthesis of sugar chains containing sialic acid.

7. A method of treating inflammation in a patient in need of treatment which comprises administering to said patient an effective amount of the sugar compound of claim 1 to prevent or reduce inflammation.

8. A sugar compound according to claim 1, wherein $R^1$ is ovalbumin.

9. A sugar compound according to claim 1, wherein $R^1$ is fetuin.

10. A sugar compound according to claim 1, wherein $R^1$ is glycophorin.

11. A sugar compound according to claim 1, wherein $R^1$ is $\alpha$2-macroglobulin.

12. A sugar compound according to claim 1, wherein $R^2$ is a tetrahydropyranyl group.

13. A sugar compound according to claim 1, wherein $R^2$ is a sulfhydryl group.

14. A sugar compound according to claim 1, wherein $R^1$ is methyl and $R^2$ is a hydrogen atom.

15. A sugar compound according to claim 1, wherein $R^1$ is a hydrogen atom and $R^2$ is a hydrogen atom.

* * * * *